(12) United States Patent
Yagi

(10) Patent No.: US 12,124,613 B2
(45) Date of Patent: Oct. 22, 2024

(54) PERSONAL DATA DISTRIBUTION MANAGEMENT SYSTEM AND PERSONAL DATA DISTRIBUTION MANAGEMENT METHOD

(71) Applicant: OSAKA UNIVERSITY, Osaka (JP)

(72) Inventor: Yasushi Yagi, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 325 days.

(21) Appl. No.: 17/771,834

(22) PCT Filed: Oct. 29, 2020

(86) PCT No.: PCT/JP2020/040568
§ 371 (c)(1),
(2) Date: Apr. 26, 2022

(87) PCT Pub. No.: WO2021/085519
PCT Pub. Date: May 6, 2021

(65) Prior Publication Data
US 2022/0374550 A1 Nov. 24, 2022

(30) Foreign Application Priority Data
Oct. 31, 2019 (JP) .................................. 2019-198139

(51) Int. Cl.
*G06F 21/00* (2013.01)
*G06F 21/62* (2013.01)
(Continued)

(52) U.S. Cl.
CPC ......... *G06F 21/6254* (2013.01); *G16H 10/60* (2018.01); *G06F 21/31* (2013.01); *G06F 21/6245* (2013.01)

(58) Field of Classification Search
None
See application file for complete search history.

(56) References Cited

U.S. PATENT DOCUMENTS 5,754,939 A * 5/1998 Herz .................. H04N 21/4622
348/E7.071
6,029,195 A * 2/2000 Herz ................ H04N 21/25891
348/E7.071
(Continued)

FOREIGN PATENT DOCUMENTS

EP 3477527 A1 5/2019
JP 2005-346248 A 12/2005
(Continued)

OTHER PUBLICATIONS

International Search Report for corresponding Application No. PCT/JP2020/040568, mailed Jan. 26, 2021.
(Continued)

*Primary Examiner* — Farhan M Syed
(74) *Attorney, Agent, or Firm* — Renner, Otto, Boisselle & Sklar, LLP

(57) ABSTRACT

A personal data distribution management system includes source data management devices, a data distribution management device, and a relay processing device that are separate devices and are connected on a network. The source data management device includes a database that stores personal data on an individual subjected to a measurement with a measuring instrument, and attribute information related to the individual and the measurement, the database storing the personal data and the attribute information as original data associated with real name information on the individual. The data distribution management device fetches original data except for personal data, and creates a data catalog. The relay processing device outputs the data, which is the data except for real name information on individuals and from the database of each source data management device based on the data usage request received from the outside, to a data user terminal. This configuration enables (Continued)

data distribution management that reduces the risk of information leakage of personal data and individual real name information.

9 Claims, 13 Drawing Sheets

(51) Int. Cl.
*G16H 10/60* (2018.01)
*G06F 21/31* (2013.01)

(56) References Cited

U.S. PATENT DOCUMENTS

| | | | | |
|---|---|---|---|---|
| 6,460,036 | B1* | 10/2002 | Herz | H04N 21/4755 |
| | | | | 348/E7.071 |
| 2003/0158960 | A1* | 8/2003 | Engberg | G06Q 30/06 |
| | | | | 709/228 |
| 2005/0138658 | A1* | 6/2005 | Bryan | H04H 60/27 |
| | | | | 725/35 |
| 2018/0225479 | A1* | 8/2018 | Yamaoka | H04L 9/0643 |
| 2019/0228180 | A1* | 7/2019 | Maeda | G06F 21/6245 |
| 2020/0159960 | A1* | 5/2020 | Jakobsson | G06F 21/6245 |

FOREIGN PATENT DOCUMENTS

| | | |
|---|---|---|
| JP | 2014-199589 A | 10/2014 |
| JP | 2018-128884 A | 8/2018 |
| JP | 2019-128681 A | 8/2019 |
| JP | 6566278 B | 8/2019 |
| JP | 6592213 B | 9/2019 |
| WO | 2005094175 A2 | 10/2005 |

OTHER PUBLICATIONS

Ryosuke Watanabe, Utilization and Management of Personal and Privacy Information in Enterprises, May 2, 2018.
Extended European Search Report for corresponding European Application No. 20882660.2, mailed Dec. 9, 2022.
Japanese Office Action for corresponding Japanese Application No. 2021-553675, mailed May 28, 2024, with Machine Translation.

* cited by examiner

FIG. 6 (A)

Name identification table

| Real name | Primary pseudonym |
|---|---|
| ○○○ | ID-a1 |
| ○▲○ | ID-a2 |
| ... | ... |
| ○○○ | ID-b5 |
| ▲○▲ | ID-b6 |

FIG. 6 (B)

Secondary pseudonym table

| Primary pseudonym | Secondary pseudonym |
|---|---|
| ID-a1 | ID1 |
| ID-b5 | ID1 |
| ... | ... |
| ID-c9 | IDn |

| Data provider | Primary pseudonym | Data Type | Attribute information | | | Number of data |
|---|---|---|---|---|---|---|
| | | | | | | |
| A | ID-a1 | ○○ | ⋮ | | | |
| A | ID-a2 | ○○ | ⋮ | | | |
| ⋮ | ⋮ | ⋮ | ⋮ | | | |
| B | ID-b5 | ○△ | ⋮ | | | |
| B | ID-b6 | ○○ | ⋮ | | | |

General Data Catalog

| Secondary pseudonym | Data type | Attribute information | | | Number of data |
|---|---|---|---|---|---|
| ID1 | ○○ | ⋮ | | | |
| ID2 | ○○ | ⋮ | | | |
| ⋮ | ⋮ | ⋮ | | | |
| IDn | ○○ | ⋮ | | | |

General Data Catalog

FIG. 8

Selected items for usage request

| Data type | ○○ |
|---|---|
| Data provider | A |
| Measuring instrument | |
| Other attribute information | |

FIG. 9 (A)

| Secondary pseudonym | Data type | Attribute information |
|---|---|---|
| ID1 | ○○ | a,b,··· |
| ID2 | ○○ | a,c,··· |
| ID3 | ○○ | a,d,··· |
| ·· | ·· | ·· |
| IDn | ○○ | a,b,··· |

Catalog information

| Response Results |
|---|
| consent |
| non-consent |
| consent |
| consent |
| consent |

FIG. 9 (B) Reassigned

| Secondary pseudonym | Pseudonym for provision |
|---|---|
| ID1 | LID1 |
| ID2 |  |
| ID3 | LID2 |
| ·· | ·· |
| IDn | LIDj |

FIG. 9 (C) Data for provision (after reassigning pseudonym)

| Pseudonym for provision | Real data | Attribute information |
|---|---|---|
| LID1 | 175 | a,b,··· |
| LID2 | 174 | a,d,··· |
| ·· | ·· | ·· |
| LIDj | 182 | ··· |

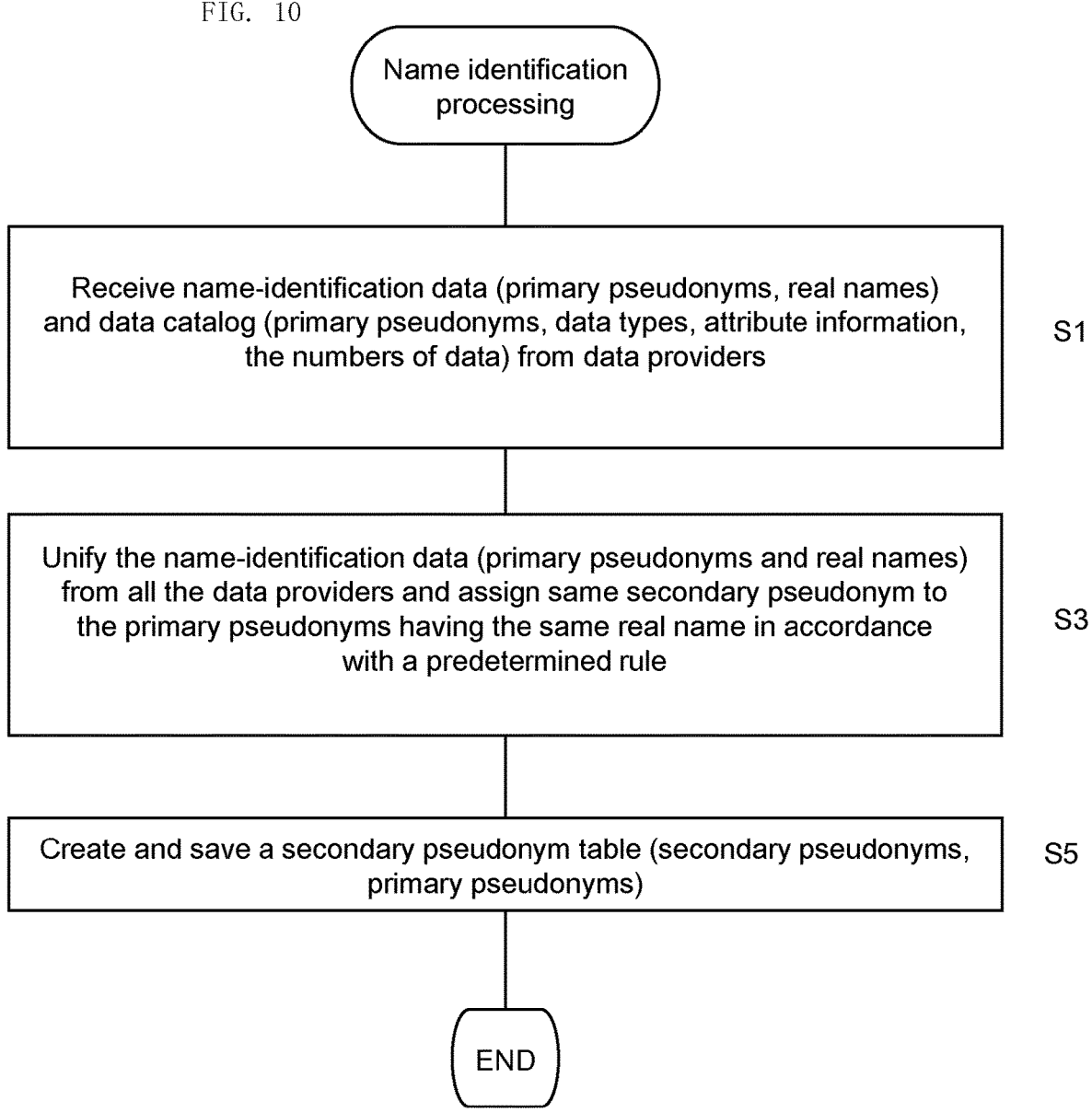

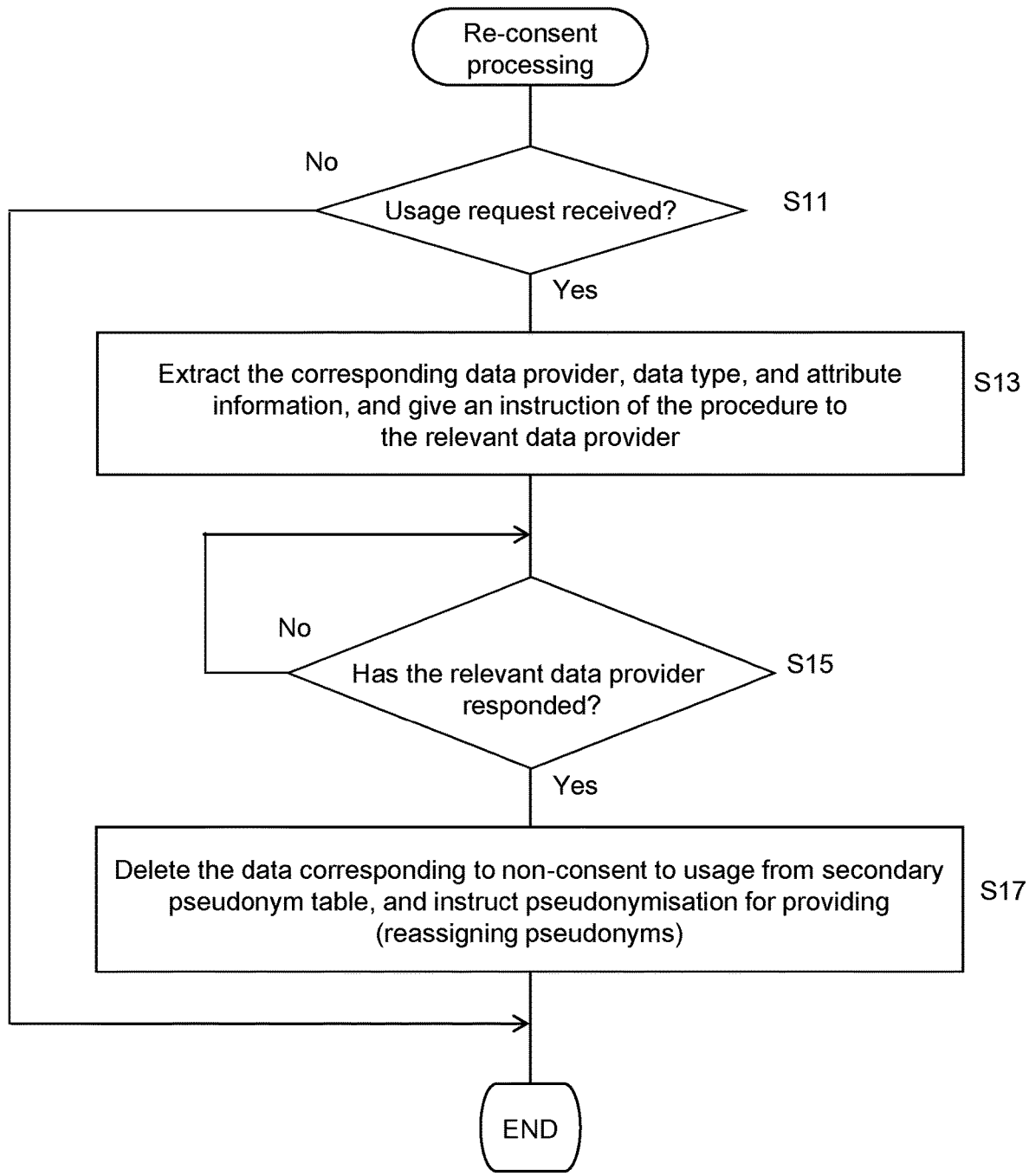

PERSONAL DATA DISTRIBUTION MANAGEMENT SYSTEM AND PERSONAL DATA DISTRIBUTION MANAGEMENT METHOD

CROSS-REFERENCE TO RELATED APPLICATION(S)

The present application is a national stage entry under 35 U.S.C. § 371 of International Application No. PCT/JP2020/040568, filed on Oct. 29, 2020, and claims the benefit of priority to Japanese Patent Application No. 2019-198139, filed on Oct. 31, 2019, the entire disclosure of which is incorporated herein by reference.

TECHNICAL FIELD

The present invention relates to techniques for personal data distribution management that manage the distribution of personal data collected from a plurality of individuals.

BACKGROUND ART

Utilization of big data is the key to achieve data-driven economic growth and social transformation. Among various types of big data, personal data in particular is attracting attention. Advantageous are expected from the use of personal data, for example, to benefit various people for medical progress and health promotion, to create a high-quality service that matches each individual better using the personal data for the target individual, and to enable highly effective marketing using personal data.

On Jun. 9, 2017, the Japanese Cabinet decided in the "Future Investment Strategy 2017" to promote three concrete measures so as to facilitate data distribution and utilization across businesses and industries in Japan. These measures are (1) linkage and utilization of industrial data, (2) utilization of personal data, and (3) promotion of digital transformation in the private sectors. In Japan, schemes such as personal data stores (PDS), information banks, and data trading markets have been proposed in order to properly utilize and protect personal data and to handle the data in a balanced manner between the utilization and the protection. As of 2019, example cases of information banks and data trading markets have begun to emerge gradually. The PDS and information banks are schemes that promote personal consent on conversion of the personal data into big data, and the data trading market is positioned as an important scheme for matching to promote distribution and utilization of the data.

Personal data is acquired by a company each time individuals use the services of the company, so that the information system managed by the company often manages and stores the data. However, the personal data originally belongs to individuals, and it is socially accepted that the individuals should store and manage the data at their own discretion and should understand the fact that the information is present. Based on this, the study has been launched to let the distribution of personal data start from the individuals (data portability). To this end, the PDS was conceived, which is a system that allows individuals to collect and manage the personal data they provide to companies at their fingertips, and to easily set the conditions of use for each piece of data. The provisions of the Personal Information Protection Law and guidelines stipulate that prior consent of the individuals is mandatory for companies to utilize the personal data, and the PDS is a scheme to systematically implement such consent of the individuals. The PDS itself is a systematic implementation of the consent of the individuals and does not include a scheme for data distribution. For companies, it is costly to obtain the consent for the utilization of personal data from each individual and collect the data. The information bank is a scheme of letting individuals set the conditions for the use of their personal data in advance and then entrust some or all of their data to a business operator that operates the information bank. By linking with the PDS, the scheme of the information bank also may execute the individuals' procedure for their right using the PDS, for example, on their behalf. Information banks provide all the services to give the data to third parties, including negotiating the price for data provided and joining different data.

The European Union (EU) established a new rule named the EU General Data Protection Regulation (GDPR), on the processing and transfer of personal data in April 2016. The idea of GDPR, which is creating a global trend, requires re-consent at the time of provision of data to a third party. The GDPR, however, is no more than comprehensive consent because the information bank is entrusted with all the data, irrespective of the purpose of data use and users. If the data distribution over the world is targeted, re-consent before providing data to a third party is essential. Note that amended act on the Protection of Personal Information defines "health and medical data" and "financial data" (credit card numbers and bank account numbers) as one of the information requiring special care. The management of such data by information banks is not covered by the "Guidelines for Certification of Information Trust Functions ver. 1.0," and it is still under consideration as public opinions have been solicited since June 2019. The "data trading market" is a data sale and purchase scheme that matches the supply and demand among the individuals who directly manage their personal data in their PDS, information banks that receive data from individuals and manage the data on their behalf, and companies (and platforms that are aggregations of multiple companies) that have needs to collect personal data for the purpose of effectively utilizing their own industrial data. The expected functions of this market include price formation/presentation for data trading, refining transaction conditions, standardization of transaction targets, and credit guarantee of transactions. To distribute personal data globally, it is useful to create the scheme of a data trading market that involves a re-consent process in the format that complies with amended act on the Protection of Personal Information and GDPR.

Meanwhile, in recent years, various systems have been proposed to realize the distribution of personal data of individuals. For example, Patent Literature 1 describes a personal data providing system including a business entity that acquires personal data of individuals, a buyer, and a broker that intervenes between the business entity and the buyer and mediates the application from the buyer and the provision of personal data to be purchased. This system assigns a temporary ID to each individual to ensure their anonymity to the broker and the buyer. Patent Literature 2 describes an intermediary device that is interposed between a plurality of information bank devices that store personal data and a data use device, and the intermediary device supports a data usage request from the data use device. Patent Literature 3 describes a personal data management system including a management server equipped with a user information storage unit and a requesting server that issues a request for user information.

A personal data management system including a management server equipped with a user information storage unit and a requesting server that issues a request for user information are described.

CITATION LIST

Patent Literatures

Patent Literature 1: JP-A-2018-128884
Patent Literature 2: JP-B-6592213
Patent Literature 3: JP-B-6566278

SUMMARY OF INVENTION

Technical Problem

Although the data management system, data providing system, and intermediary device described in Patent Literatures 1 to 3 include a source data storage unit storing personal data, they do not include a distribution management device that creates and stores a catalog for promoting the distribution of personal data. Moreover, when a system is configured to include a data distribution management device and multiple source data storage units separately, it is not easy to design the system as a whole to manage the information security of personal data, comply with GDPR, and protect personal information.

In view of the above, the present invention provides personal data distribution management system and method that are capable of managing personal data distribution while reducing the risk for information leakage of personal data.

The present invention also provides personal data distribution management system and method that enable data distribution management while protecting personal information such as real names and complying with GDPR.

Solution to Problem

A personal data distribution management system according to the present invention includes at least one source data management device, a data distribution management device, and a relay processing device that are separate devices and are connected on a network. The source data management device includes a database that stores personal data on an individual subjected to a measurement with a measuring instrument, and attribute information related to the individual and the measurement, the database storing the personal data and the attribute information as original data associated with real name information on the individual. The data distribution management device includes a usage request receiving module that receives a data usage request from a data user terminal. The relay processing device selects personal data on an individual corresponding to the data usage request from the database of each source data management device based on the data usage request that the usage request receiving module receives, and outputs the selected personal data except for real name information on the individual to the data user terminal.

A personal data distribution management system according to the present invention includes at least one source data management device, and a data distribution management device that are separate devices and are connected on a network. The source data management device includes a database that stores personal data on an individual subjected to a measurement with a measuring instrument, and attribute information related to the individual and the measurement, the database storing the personal data and the attribute information as original data associated with real name information on the individual. The data distribution management device includes a catalog management module configured to fetch the original data except for the personal data, the original data being stored in the database of each source data management device, and unify and edit the fetched data to create a data catalog.

A personal data distribution management method according to the present invention includes creating original data by associating personal data on an individual subjected to a measurement with a measuring instrument and attribute information related to the individual and the measurement with real name information on the individual and storing created data in a database, by at least one source data management device, receiving a data usage request from a data user terminal by a data distribution management device, and selecting personal data on an individual corresponding to the data usage request from the database of the at least one source data management device based on the data usage request that the data distribution management device receives, and outputting selected personal data except for real name information on the individual to the data user terminal, by a relay processing device. The at least one source data management device, the data distribution management device, and the relay processing device are separate devices and are connected on a network.

According to these aspects of the present invention, the data distribution management device fetches original data except for personal data, and creates a data catalog. The relay processing device outputs the data, which is the data except for real name information on individuals and from the database of each source data management device based on the data usage request received from the outside, to a data user terminal. This configuration enables data distribution management that reduces the risk of information leakage of personal data and individual real name information from the database of each source data management device to the outside.

Advantageous Effects of Invention

The present invention enables data distribution management that reduces the risk of information leakage of personal data and individual real name information.

BRIEF DESCRIPTION OF DRAWINGS

FIG. 5A shows the items on a data provider and its email address and FIG. 5B shows the items on the individual's real name and personal attribute information.

FIG. 6A and FIG. 6B describe an example of the name identification process, and FIG. 6A shows a name identification table, and FIG. 6B shows a secondary pseudonym table.

FIG. 7A shows a general data catalog and FIG. 7B shows an edited catalog.

FIG. 8 describes an example of selected items in a data usage request.

FIG. 9A and FIG. 9B describe the final pseudonymization process, and FIG. 9A shows a data catalog, FIG. 9B shows an example of reassignment, and FIG. 9C shows data for provision.

FIG. 10 is a flowchart showing an example of the name identification processing performed by the data distribution management device.

FIG. 11 is a flowchart showing an example of the re-consent processing performed by the data distribution management device.

DESCRIPTION OF EMBODIMENTS

Figure 1:
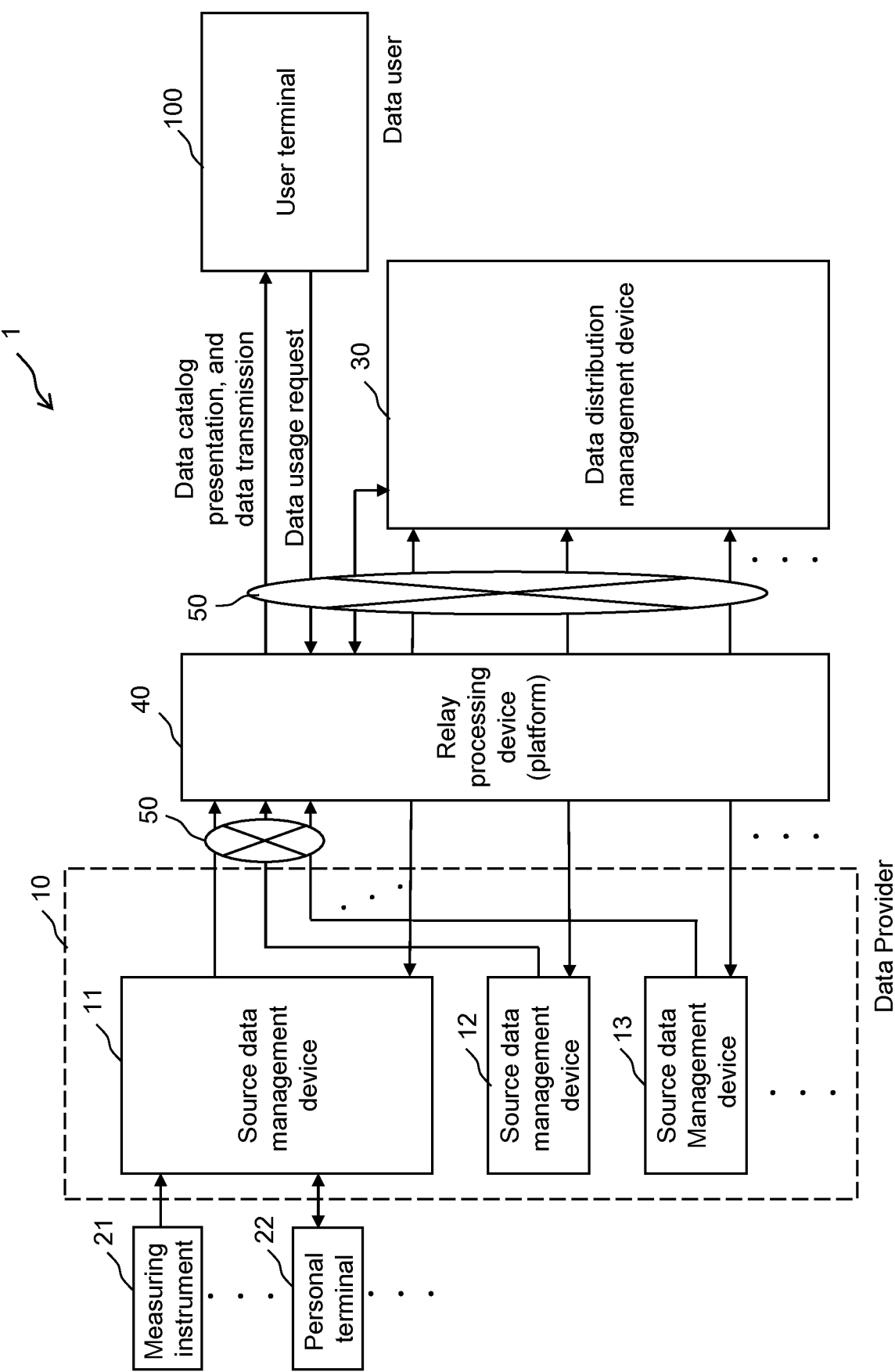
FIG. 1 shows a configuration of a personal data distribution management system that is one embodiment according to the present invention.

FIG. 1 shows a configuration of a personal data distribution management system that is one embodiment according to the present invention. In FIG. 1, the personal data distribution management system 1 includes a data provider 10, a data distribution management device 30, and a relay processing device 40 that functions as a platform, and they are data communicable via a network 50 such as the internet. The personal data distribution management system 1 is connectable to a user terminal 100 via the network 50.

The data provider 10 includes at least one source data management devices 11, 12, 13, ..., which are units that collect and store one group of data sets. For these source data management devices 11, 12, 13, ..., a corporation, a company, a university corporation, an organization, and an individual are assumed. In this embodiment, they are hospital units or may include medical office units. The individual or diagnostic personal data in the present embodiment may include various vital data such as heart rates and blood pressure, and data types such as purchase history information in the hospital. The present embodiment assumes that each entity of the data provider 10 and the user terminal 100 is a member who has joined the organization of this system, but this is not always essential. Members are given an ID and a password, based on which they can receive data viewing and usage request services.

The following describes an overview of the data distribution management process executed by the personal data distribution management system 1. The source data management devices 11, 12, 13, ... making up the data provider 10 each collect personal data from a plurality of individuals (e.g., patients and examinees). Various types of personal data are assumed. The collected personal data of various types is associated with real name information and is stored in units of the source data management devices 11, 12, 13, ... of the data provider 10. Note that, hereinafter, the personal data refers to various types of data obtained from an individual, the real name information refers to information that can identify a specific individual, and personal attribute information refers to gender, age, email address, address, and the like.

The data distribution management device 30 functions as a data trading market, creating promotional data catalogs to promote data distribution (purchase and sales of personal data of individuals) and providing them to be viewable on the network 50. When receiving a data usage request from a third party via the network 50, the data distribution management device 30 searches for personal data that corresponds to the content of the usage request and performs re-consent procedure processing to the parties involved and individuals, and then provides the data to the user under predetermined conditions (benefit). Examples of the benefit may include money and points as well as various services and other forms of compensation.

In this example, the system performs first and second pseudonymization to prevent the individuals from being identified, and when providing the personal data, performs reassignment of anonymity (pseudonymization for provision) so that the data cannot be restored, and provides it to the third party together with the real data. When re-consent is obtained from an individual who provided personal data under a predetermined condition before data use by the third party, the re-consent may be required also from those involved in the data collection. In this case, the system effectively performs re-consent procedure processing in a predetermined priority. The details are described below.

Figure 2:
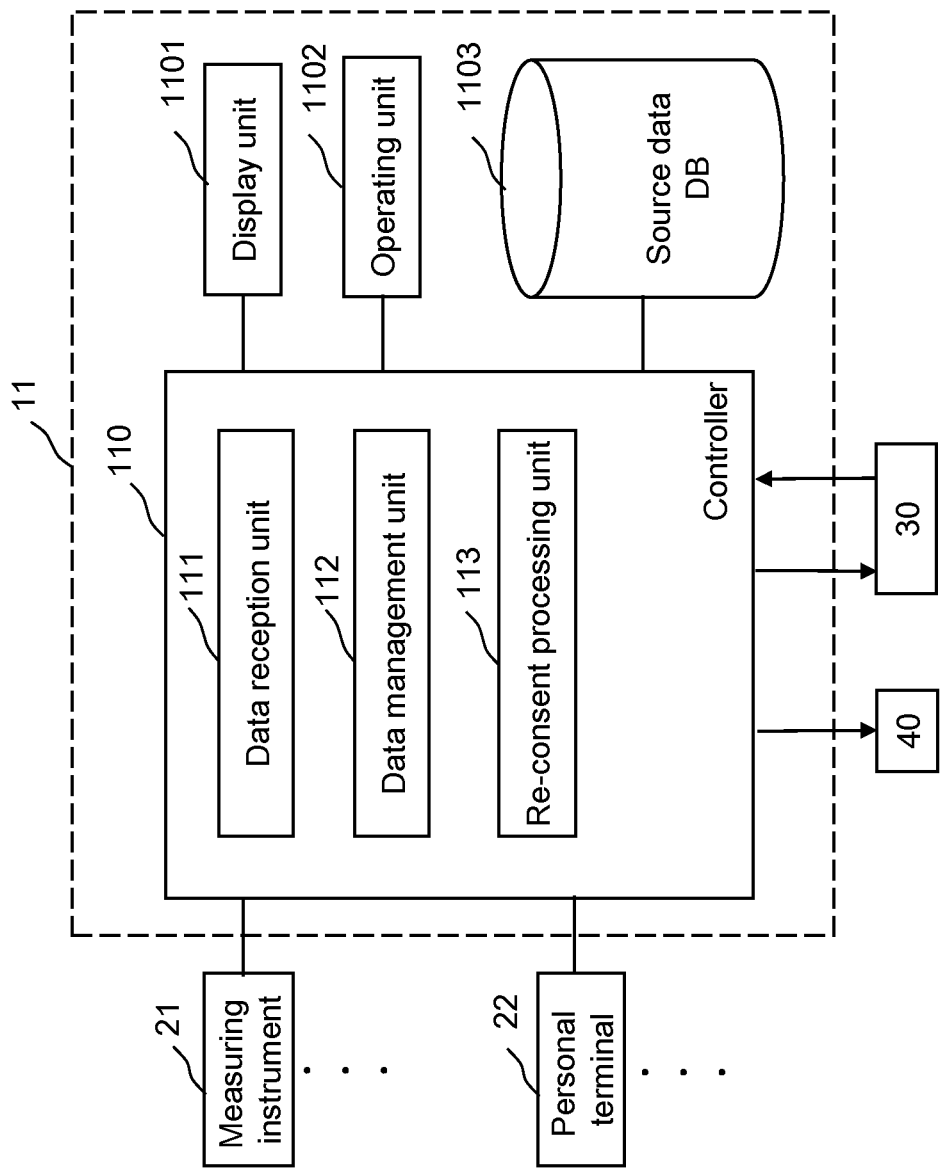
FIG. 2 shows the configuration of a source data management device that is one embodiment.

FIG. 2 shows a configuration of the source data management device 11 that is one embodiment. The source data management devices 11, 12, 13, ... have the same configuration, and the following describes the source data management device 11 as one example. The source data management device 11 has a controller 110 including a processor (CPU). The controller 110 is connected to a display unit 1101 that displays an image, an operating unit 1102 to input information, instructions and the like from the outside, and a source data DB 1103 that stores predetermined data.

In the present embodiment, a measuring instrument 21 measures various vital data, which is personal data, from individuals. In one example, the measuring instrument 21 includes a heart rate monitor, a sphygmomanometer, and various sensors, instruments, and devices such as an MRI for measuring (imaging) the interior of a living body. The personal terminal 22 includes a personal computer, a smartphone, and various other mobile information and communication terminals, which exchanges information using SNS (Social Network System), SMS (Short Message Service), or e-mail.

Figure 5:
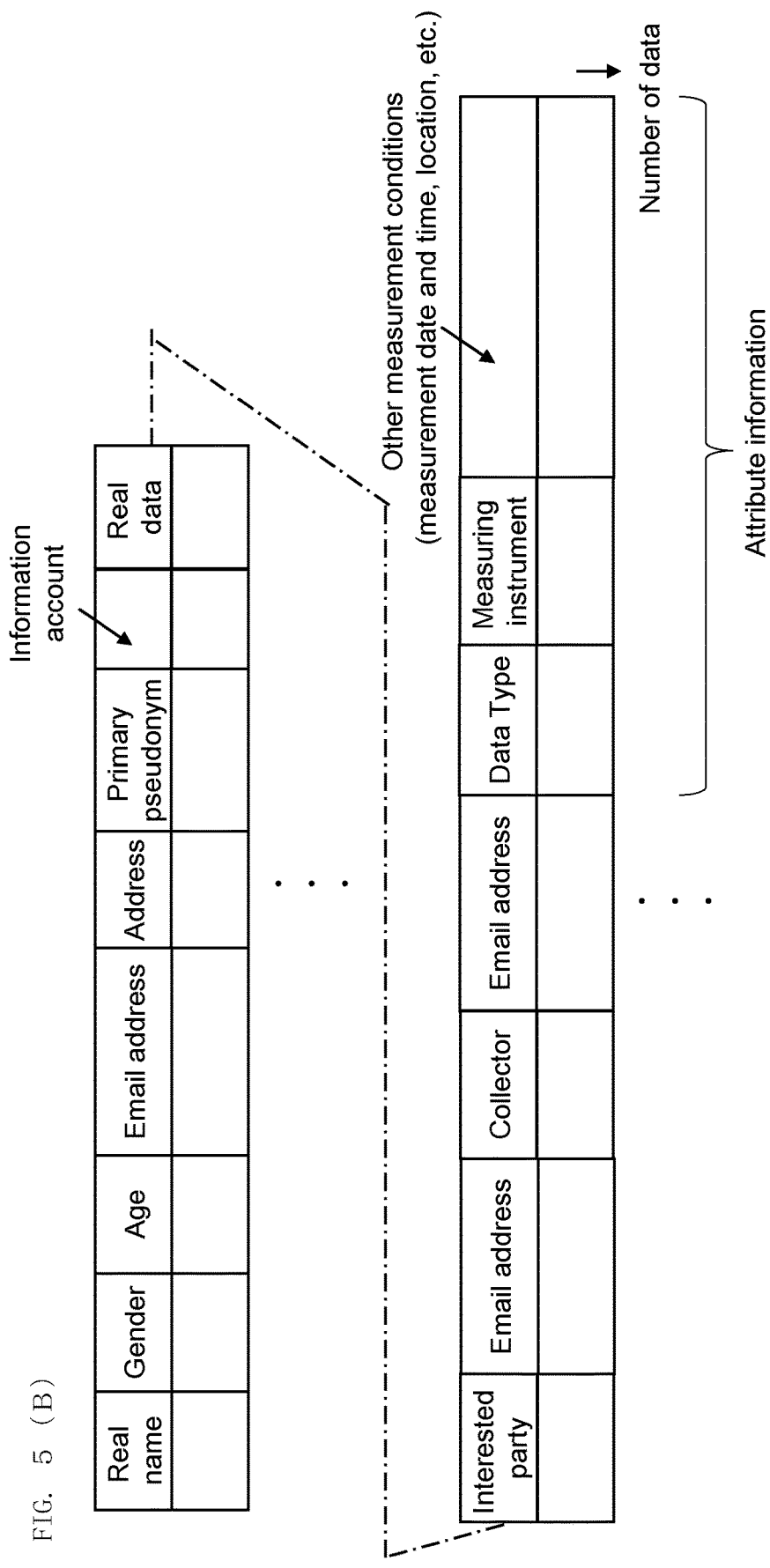
FIG. 5A and FIG. 5B each are a memory map showing an example of original data items.

The source data DB 1103 stores a control program that controls the source data management process performed by the controller 110, as well as original data including personal data, which is the real data on multiple individuals measured with the measuring instrument 21. FIG. 5A and FIG. 5B each are a memory map showing an example of items of the original data. FIG. 5A shows the item on the data provider, that is, one of the data set units, hospital "A" in this embodiment. The memory map in this embodiment then has the item of e-mail address of hospital A. As shown in FIG. 5B, following the item of the individual's real name, this memory map has the items of the individual's gender, age, email address as above, address, primary pseudonym, information account, and real data (personal data) that are attribute information on the individual. The primary pseudonym refers to identification information that is automatically assigned according to an individual's real name, typically according to an appropriate rule, when the original data is created at hospital "A". The information account is an account for managing an individual on the system and contains the location information. This information account refers to the location where benefits are accumulated that are updated each time the individual's personal data is provided.

The original data may have other information items as needed. In this embodiment, they are items of attribute information on persons involved in the measurement such as an interested party and a collector, and their e-mail addresses. The items of information account may also be prepared for these interested party and collector. In one example, the interested party is the provider of the measuring instrument or measuring location, and the collector is the person who was engaged in the measurement work. Other attribute information may include a data type, a measuring instrument (model name, etc.), and various other measurement conditions (e.g., measurement date and time, measurement location). In principle, the benefit is borne by the data user, but the data distribution management device 30 may partially bear the benefit or pay it in advance. The content of the benefit may be set in advance, or it may be determined through negotiation each time an application for data use is made.

Through the execution of a control program by the processor, the controller 110 functions as a data reception unit 111, a data management unit 112 and a re-consent processing unit 113.

The data reception unit 111 performs a process of registering various types of data in the original data table for each individual as shown in FIG. 5A and FIG. 5B via the operating unit 1102 or automatically registering the data for some items. For example, the measurement data with the measuring instrument 21, which is the personal data, may be associated with an individual's primary pseudonym, and automatically input. In this case, the consent of each individual and, if necessary, of the interested party and the collector is obtained about the utilization (primary use) of personal data at the data provider 10 or at hospital "A".

The data management unit 112 performs data management as follows based on the original data shown in FIG. 5A and FIG. 5B. The data management unit 112 creates source data (primary pseudonyms and personal data) having pairs of primary pseudonyms and personal data that is real data, excluding the real name information, and the source data is to be uploaded (or linked) to the relay processing device 40. This source data (primary pseudonyms, personal data) may be stored in the relay processing device 40 or in the source data management device 11.

The data management unit 112 also creates a table for name identification (primary pseudonyms and real names) having pairs of primary pseudonyms and real names, excluding the personal data, and the table for name identification is data to be submitted to the data distribution management device 30. The data management unit 112 also associates a data catalog (providers, data types, attribute information including measuring instruments and other measurement conditions, and the numbers of data) having a group of providers, data types, attribute information, and the numbers of data, excluding the personal data, with their primary pseudonyms to create data to be submitted to the data distribution management device 30. The data management unit 112 creates the data at the startup of the source data management device 11 or at other appropriate times, and sends the created data to the data distribution management device 30. The table for name identification (hereinafter called a name identification table) is stored in a name-identification data DB 341 of the data distribution management device 30. The data catalog is stored in a data catalog DB 342 of the data distribution management device 30.

The re-consent processing unit 113 executes the process for re-consent that the source data management device 11 handles. The re-consent processing is a procedure to, in response to a data usage request from the user terminal 100 that is a third party, obtain a consent form for the data use (secondary use) from the individual whose personal data corresponds to the content of the request and, if necessary, from the data provider, the interested party and the collector in the attribute information. As described later, this re-consent processing is performed by the instruction from the data distribution management device 30, typically electronically and via network 50. In some cases, other means of communication may be used for this purpose.

In this embodiment, the re-consent procedure is performed in accordance with a predetermined priority order. Specifically, the priority is in the order of the data provider, the interested party and the collector, and finally the individual. When receiving an electronic re-consent application form, the re-consent processing unit 113 operates the operating unit 1102 to fill the marks in the check boxes on the re-consent application form to give a reply for instruction. The check boxes are provided corresponding to the required units, and indicate consent or non-consent.

If the source data management device 11 does not consent, the re-consent processing ends. In contrast, if it consents, the re-consent processing unit 113 sends a re-consent application form for the interested party and the collector received at the same time to the relevant interested party right and collector. In this embodiment, the re-consent processing unit 113 sends the application form by e-mail, and waits for a response (reply). The re-consent processing unit 113 finishes the procedure for the data when the response from the interested party and the collector indicates non-consent, while, for the case of consent, sends a re-consent application form for individuals to the relevant individual by e-mail, and waits for a response (reply). Setting such a priority order enables effective re-consent procedure. Note here that the interested party and the collector, and the individual will be given benefit in various forms for the re-consent. In one example, their benefit is paid to the information account shown in FIG. 5A and FIG. 5B as described above. Other forms of re-consent and methods of processing re-consent are described below.

Figure 3:
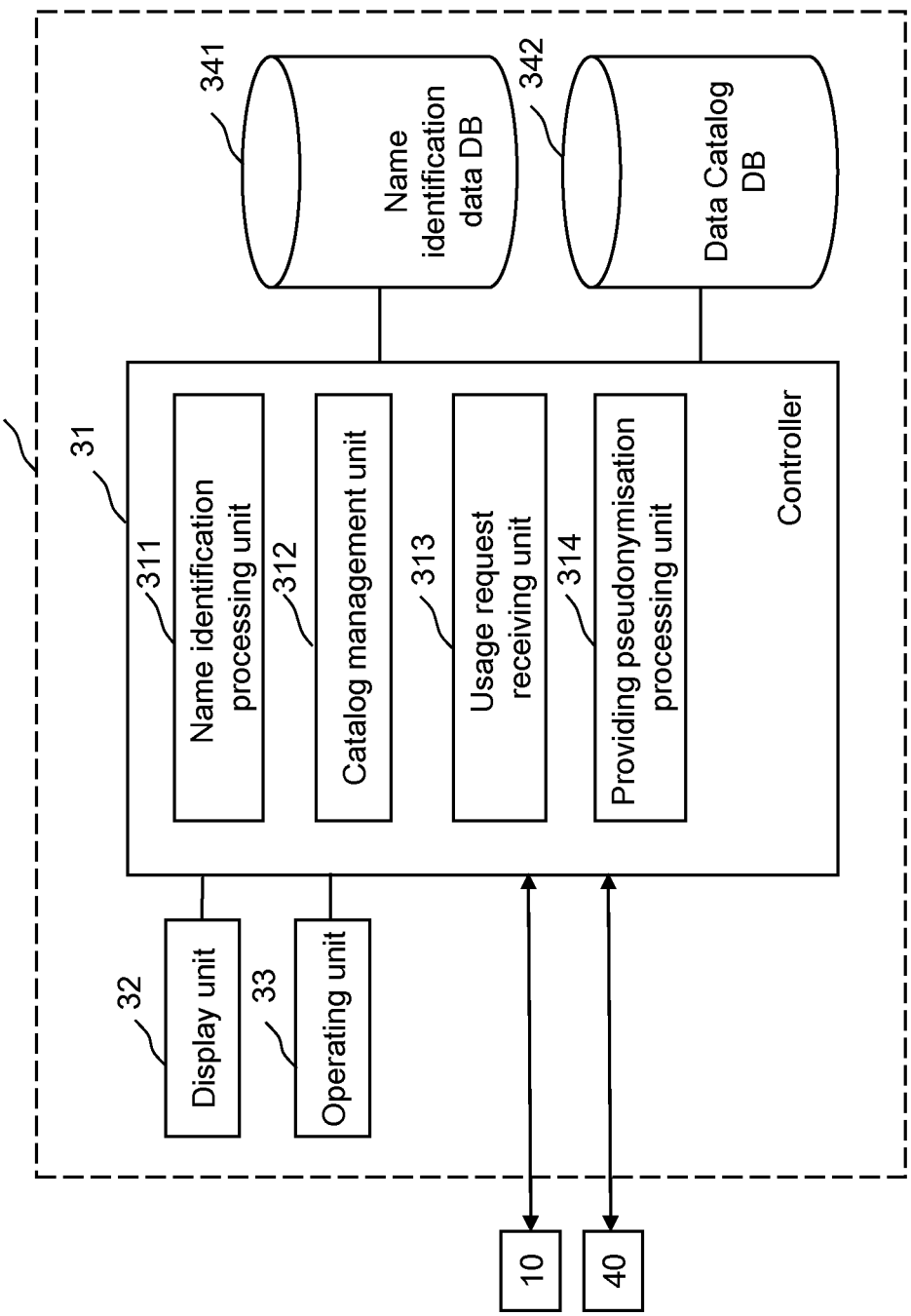
FIG. 3 shows the configuration of a data distribution management device that is one embodiment.

FIG. 3 shows the configuration of the data distribution management device 30 that is one embodiment. The data distribution management device 30 has a controller 31 including a processor (CPU). The controller 31 is connected to a display unit 32 that displays an image, an operating unit 33 to input information, instructions and the like from the outside, a name-identification data DB 341 that stores data for name identification, and a data catalog DB 342 that stores a data catalog. The control program for data distribution management may be written in the program storage areas in these memories.

Through the execution of a control program by the processor, the controller 31 functions as a name-identification processing unit 311, a catalog management unit 312, a usage request receiving unit 313, and a providing pseudonymization processing unit 314.

As shown in FIG. 6A and FIG. 6B, the name-identification processing unit 311 creates a secondary pseudonym from the name identification table (primary pseudonyms, real names) stored in the name identification data DB 341, and stores it in the name identification data DB 341. Specifically, the name-identification processing unit 311 unifies (integrates) the name identification tables (primary pseudonyms and real names) from the source data management devices 11, 12, 13, . . . (see FIG. 6A), performs name-identification processing to match real names and primary pseudonyms, creates integrated secondary pseudonyms from the primary pseudonyms, and stores the created secondary pseudonym table (see FIG. 6B) in the name-identification data DB 341. When transmitting the name identification table (primary pseudonyms, real names) to the data distribution management device 30, the source data management devices 11, 12, 13, . . . transmit the data via a network other than the network 50 or by another communication method, thus lowering the risk of leakage of real name data during communication. In the example of FIG. 6A and FIG. 6B, the primary pseudonym ID-a1 of the individual who was treated at hospital "A" and the primary pseudonym ID-b5 of the individual who was treated at hospital "B" are for the same person having the common real name, and a common secondary pseudonym ID1 was reassigned to this individual in FIG. 6B. In another example, the secondary pseudonym may be a consecutive personal number. A table (secondary pseudonyms, real names) may be used as the secondary pseudonym table of FIG. 6B.

Figure 7:
FIG. 7A and FIG. 7B describe an example of the catalog management process.

As shown in FIG. 7A and FIG. 7B, the catalog management unit 312 unifies and integrates the data catalogs from the source data management devices 11, 12, 13, . . . stored in the data catalog DB 342 to create a general data catalog. In FIG. 7A and FIG. 7B, the data catalog (the provider, attribute information including data types and other information, the numbers of data), which is associated with the primary pseudonyms, is associated with the secondary pseudonyms with reference to FIG. 6B, and is edited based on the items of the data type (see FIG. 7B). Then, a part of the general data catalog is provided on the network 50 for viewing. The data catalog can be sorted based on a part or all of the data items in the browsing range, which is convenient for the user to choose the items. Instead of the sales form of providing the data catalog on the network 50, another form also is possible, including using the data catalog for sales by humans or posting it on other media.

The usage request receiving unit 313 receives a usage request from the user terminal 100 and executes processing according to the content of the request. In one example, as shown in FIG. 8, the requested content is designated based on the data items. The example of FIG. 8 assumes the data type, data provider, and other attribute information including the measuring instrument. In another mode, an example of other attribute information requested may include the gender and age group of the individual attribute information. The usage request receiving unit 313 selects a target person whose re-consent is to be solicited based on the content of the request. For example, when the requested content includes a data provider, the re-consent process may be executed only for the relevant source data management device. If not specified, all the source data management devices involved will be targeted. The usage request receiving unit 313 sends the information of the requested content to the source data management device as the target through the relay processing device 40 in this example, and instructs it to perform the re-consent process. The above-mentioned re-consent processing unit 113 may execute the selection of the target interested party, collector, and individuals, or the usage request receiving unit 313 may execute this process and send the result of selection in association with an instruction for the re-consent processing.

The providing pseudonymization processing unit 314 edits the original data in association with the secondary pseudonyms and excluding the item of real names, which is uploaded in the relay processing device 40 described later, to create data to be provided to the user who has made a usage request. Specifically, the providing pseudonymization processing unit 314 executes the process of deleting persons who do not consent to the re-consent application form from the primary and secondary pseudonym tables in FIG. 6B, reassigning pseudonyms for reporting to secondary pseudonyms remaining after the deletion, and extracting the secondary pseudonyms with which the pseudonyms for reporting are associated from the original data uploaded to the relay processing device 40 to create data for provision.

In one example, as shown in FIG. 9A, FIG. 9B and FIG. 9C, the process of reassigning pseudonyms for reporting executes predetermined sorting process to the remaining secondary pseudonyms after deletion among the secondary pseudonyms associated in the data catalog, and then replaces the secondary pseudonyms with individual identification information one by one from the top (see the table in FIG. 9B). The individual identification information can be a character code that is assigned according to a predetermined rule, for example, a serial number. In FIG. 9B, the person having the secondary pseudonym ID2 (having "attribute information: a, c, . . . ") does not consent to the application (see FIG. 9A, response: non-consent). After reassignment, the information on this person has been deleted as shown in the table for provision in FIG. 9C. The data for provision shown in FIG. 9C is edited by the relay processing device 40 based on the table after reassigning of FIG. 9B. The edited data for provision is sent from the relay processing device 40 to the user terminal 100.

Figure 4:
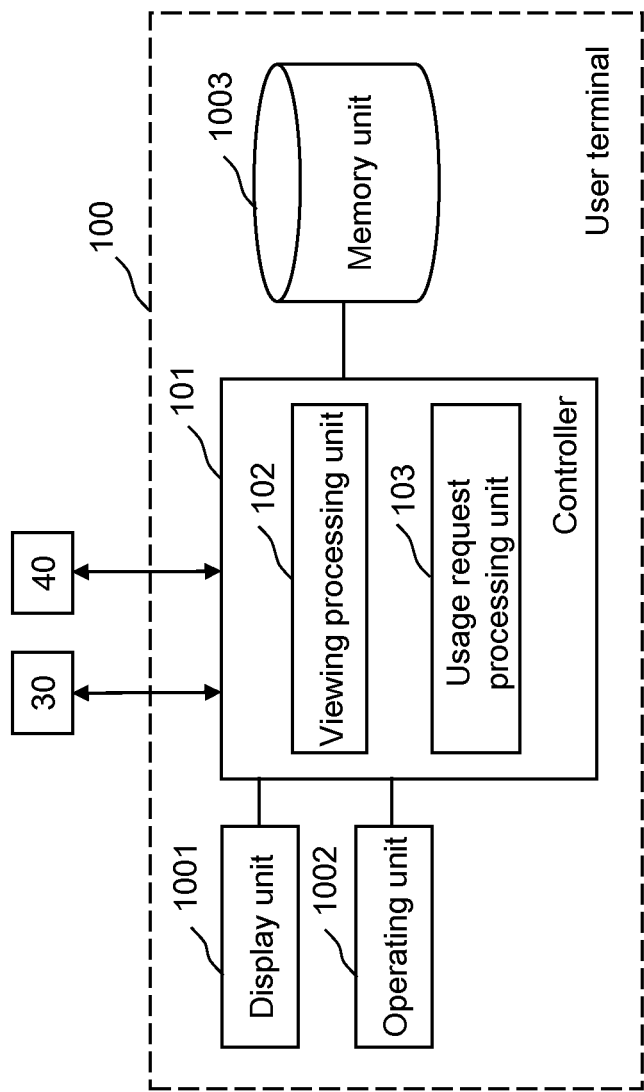
FIG. 4 shows the configuration of a user terminal that is one embodiment.

FIG. 4 shows the configuration of the user terminal 100 that is one embodiment. The user terminal 100 has a controller 101 including a processor (CPU). The controller 101 is connected to a display unit 1001 that displays an image, an operating unit 1002 to input information, instructions and the like from the outside, and a memory unit 1003 that temporarily stores the data for provision. The memory unit 1003 stores a control program (installed application program) for the personal data usage process. The user terminal 100 does not have to be a dedicated device for this system, and a general-purpose personal computer device with the application program installed can be used as long as it is communicable via the network 50. This may also be a mobile terminal.

Through the execution of a control program by the processor, the controller 101 functions as a viewing processing unit 102 and a usage request processing unit 103.

The viewing processing unit 102 transmits a viewing request for data catalog to the relay processing device 40 or the data distribution management device 30, and receives the data catalog in a viewable form under predetermined conditions (for example, being a member).

The usage request processing unit 103 transmits an electronic usage request form (usage application form) including the selected items related to the personal data that the user wants to use to the data distribution management device 30 via the relay processing device 40. The viewing process for the data for provision will be returned from the system 1 by e-mail, for example, in response to the usage request, and this process is the same as the processing for typical e-mail. The description therefore will be omitted.

Next, the procedures of name identification processing, re-consent processing, and re-consent procedure processing will be described.

FIG. 10 is a flowchart showing an example of the name identification processing performed by the controller 31 of the data distribution management device 30. First, when the controller 31 confirms predetermined timing for creating a catalog by timing with a built-in timer, for example, the controller 31 receives source data (primary pseudonyms, real names) and data catalog (primary pseudonyms, data types, attribute information, the numbers of data) from the source data management devices 11, 12, 13 . . . that are data providers (step S1). Next, the controller 31 unifies the source data (primary pseudonyms and real names) from all the data providers and assigns the same secondary pseudonym to the primary pseudonyms having the same real name in accordance with a predetermined rule (step S3). Then, the controller 31 creates and saves a secondary pseudonym table (secondary pseudonyms, primary pseudonyms) as shown in FIG. 6B based on the assigned secondary pseudonyms (step S5).

FIG. 11 is a flowchart showing an example of the re-consent processing performed by the controller 31 of the data distribution management device 30. First, the controller 31 determines the presence or not of a usage request (step S11). In the case of no usage request, the controller 31 exits this flow, and if a usage request is present, the controller 31 extracts the corresponding data provider, data type, and attribute information from the usage request form, and gives an instruction of the procedure to the relevant data provider (step S13). At this time, the data providers that are not a target for request are excluded.

Next, the controller 31 determines the presence or not of a response to the usage request from the relevant data provider (step S15). Then, the controller 31 deletes the information on the secondary pseudonyms that did not consent to the usage request by referring to the secondary pseudonym table, and reassigns the pseudonyms for provision to the remaining secondary pseudonyms (step S17). The reassignment to pseudonyms for provision anonymizes the individual corresponding to the data for provision. The reassignment to the pseudonym for provision does not guarantee that the individual with the same pseudonym for provision is the same person for each usage request, which means that even if the data is used multiple times, the individual cannot be identified. If the data provider itself responds that they do not consent, all of the following interested party, collector and individual will be handled as non-consent.

Figure 12:
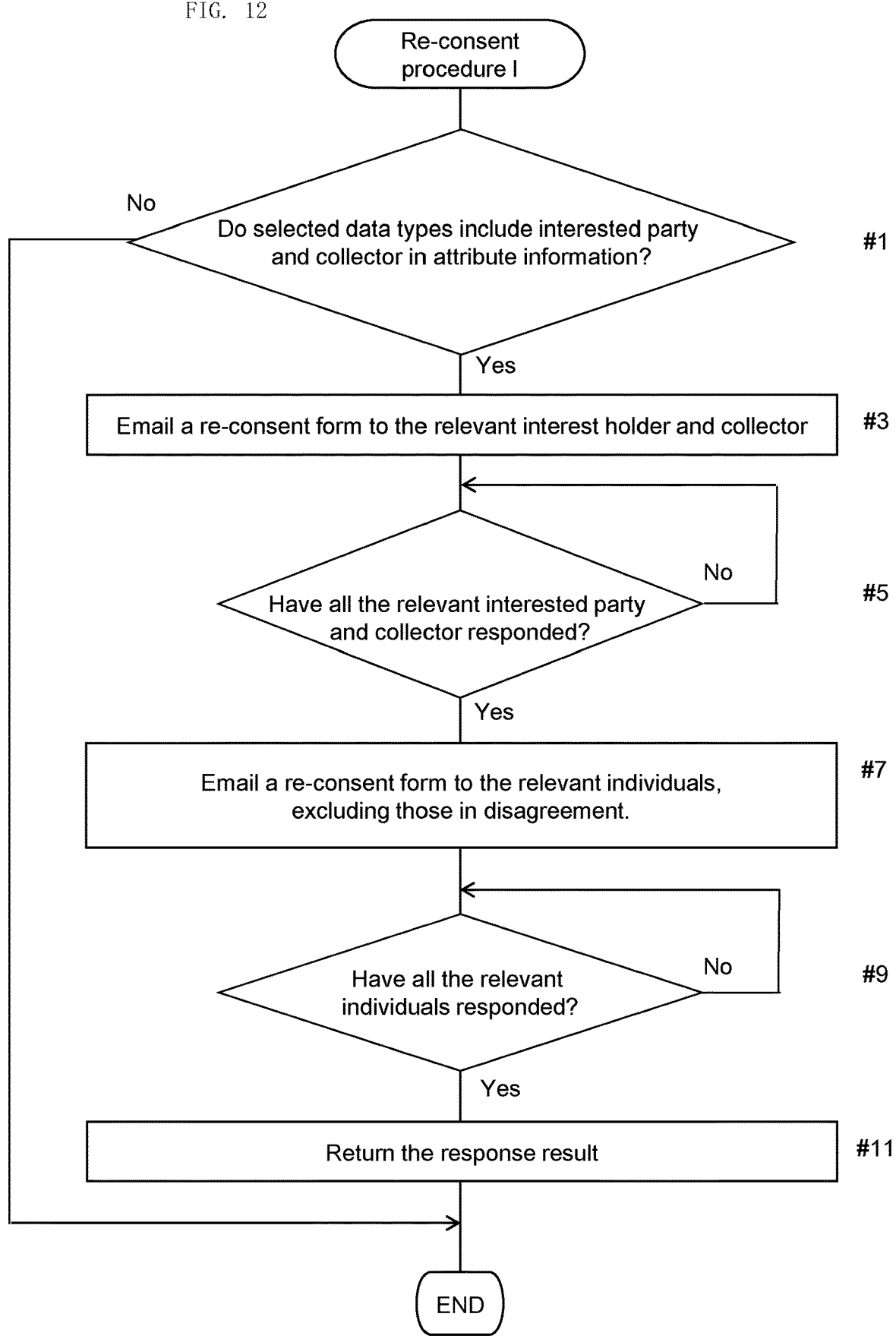
FIG. 12 is a flowchart showing an example of the re-consent procedure processing I performed by the data provider device.

FIG. 12 is a flowchart showing an example of the re-consent procedure processing I performed by the controller 110 of the source data management device 11. When receiving an instruction for re-consent procedure process from the data distribution management device 30 via the relay processing device 40, the controller 110 controls the operating unit 1102 to enter consent or non-consent to the re-consent application form for its own data provider. In the case of non-consent, the controller 110 sends it back as it is and does not enter this flow.

In contrast, in the case of consent, the controller 110 determines whether the data type selected for the usage request includes the interested party and the collector in the attribute information on the persons involved in the measurement (step #1). If no person corresponds to the case, the controller 110 exits this flow, and if an applicable person is present, the controller 110 sends a re-consent form by e-mail to the relevant interested party and collector (step #3).

Next, the controller 110 determines whether responses have been received from all the relevant interested party and collector (step #5). The controller 110 waits for responses from all the relevant interested party and collector, and then excludes the responses of non-consent, and e-mails a re-consent form to the remaining relevant individuals (step #7). The controller 110 determines whether responses have been received from all the relevant individuals (step #9). Then, the controller 110 returns the response result to the data distribution management device 30 (step #11).

Next, the following describes other embodiments of re-consent, to which the present invention is applicable. The above embodiment describes a method of handling re-consent as each-time re-consent, and determining whether or not to consent data provision in response to a usage request from a user. The present invention is not limited to this embodiment, and may be in the form of comprehensive re-consent where the consent is obtained beforehand.

The comprehensive re-consent may include a partially comprehensive re-consent and a partial batch re-consent. The comprehensive re-consent refers to permitting (setting) of re-consent in advance for all the data items (including items such as attribute information) of the original data shown in FIG. 5A and FIG. 5B. The partially comprehensive re-consent refers to permitting of re-consent in advance for certain one or more data items of the original data. The partial batch re-consent refers to permitting of re-consent in advance for a plurality of certain data items, as a batch, of the original data.

The items for which comprehensive re-consent can be set correspond to the data items that are the target of a usage request by a user in the original data. Referring to FIG. 5B, they may include "data type" and "real data" as well as "gender", "age", "measuring instrument", and various items in "other measurement conditions". This also may include the "data provider". Specifically, for example, the item of "re-consent" is set for each of these target data items. In one example, each "re-consent" item is set to alternately switch between "comprehensive" and "each-time" in an either-or choice manner. Then, the re-consent processing unit 113 of the source data management device 11 refers to the settings of each of these comprehensive re-consent items when requesting a re-consent. Details will be described with reference to FIG. 13. In another setting mode, items may be prepared separately for comprehensive re-consent, partially comprehensive re-consent, and partial batch re-consent. Then, the comprehensive re-consent may be set in an either-or choice manner, the partially comprehensive re-consent may be set by logical OR of the desired input items, and the partial batch re-consent may be set by logical product of the desired input items.

The data management unit 112 of the source data management device 11 receives requests for comprehensive re-consent from individuals, the right holder and the collector about "comprehensive" and "each-time" (including cancellation from "comprehensive") to select "comprehensive" or "each-time" for the items of "re-consent". Each item for comprehensive re-consent may be set at the time of acquisition of real data, or may be changed at any time thereafter. The data management unit 112 of the source data management device 11 may assign an ID or the like to the individual, the interested party, and the collector in advance or authorize them to rewrite the settings from their e-mail addresses so as to let them rewrite the items of comprehensive re-consent for themselves.

Figure 13:
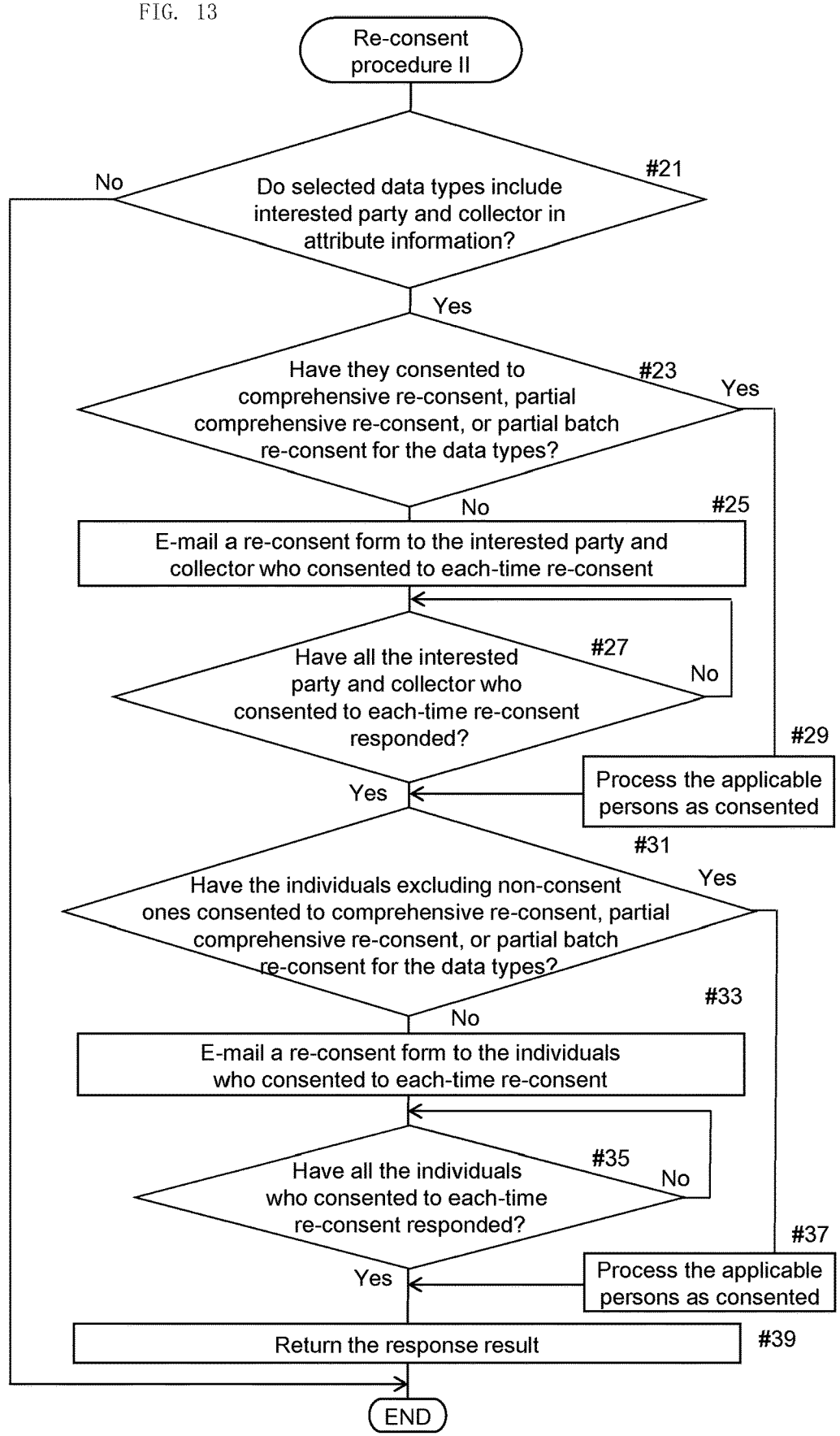
FIG. 13 is a flowchart showing an example of the re-consent procedure processing II performed by the data provider device.

FIG. 13 is a flowchart showing an example of the re-consent procedure processing II performed by the controller 110 of the source data management device 11. FIG. 13 shows a re-consent procedure including the process corresponding to the settings of the comprehensive re-consent items in addition to the flowchart of FIG. 12. Specifically, this flowchart is different in steps #23 to #37 that are added or modified, and the other steps are the same as those in FIG. 12.

Step #23 searches for the interested party and collector who have consented to comprehensive re-consent, partially comprehensive re-consent, and partial batch re-consent for the type of data for which the use request was made. Then, the procedure skips step #25 and step #27 for the searched one or more corresponding persons, and proceeds to step #29 where the searched persons are processed as having consent. For the interested parties and the collectors who correspond to the each-time re-consent in step #25, the procedure sends a re-consent form, and waits for a reply (step #27). Then, the persons who have consented to the comprehensive re-consent and to each-time re-consent are put together and the procedure proceeds to step #31.

Next, step #31 excludes the persons of non-consent, and then searches for the individuals who have consented to the comprehensive re-consent, partially comprehensive re-consent, and partial batch re-consent for the data type for which the use request was made. Then, the procedure skips step #33 and step #35 for the searched one or more individuals, and proceeds to step #37 where the searched corresponding persons are processed as having consent. For the individuals who have consented to the each-time re-consent in step #33, the procedure sends a re-consent form and waits for a reply (step #35). Then, the individuals who have consented to the comprehensive re-consent and to the each-time re-consent are put together and the procedure proceeds to step #39. In this way, comprehensive re-consent, for example, is acquired in advance, which omits the work of sending and returning the consent form to the corresponding persons, and makes the procedure more smoothly.

The source data is not limited to (provider pseudonyms, personal data), and may include items corresponding to the usage request and some pieces of attribute information of the individual, such as gender and age.

This system 1 is configured so that real name information and real data are possessed only by the corresponding source data management devices 11, 12, 13, . . ., that is, the data distribution management device 30 functioning as the trading market does not possess the real data and the relay processing device 40 does not possess the real name information. In this way, the original data is possessed in a distributed manner, which reduces the security risk greatly as compared with the configuration where the data is possessed in one place and the information is leaked therefrom. Further, neither the data distribution management device 30 nor the relay processing device 40 possesses the real name information and the real data at the same time, which means that the personal data of each individual is not identified from these devices. Also, each device may be managed by a separate organization. This suppresses their individual legal damage.

As described above, the personal data distribution management system according to the present invention includes at least one source data management device, a data distribution management device, and a relay processing device that are separate devices and are connected on a network. The source data management device includes a database that stores personal data on an individual subjected to a measurement with a measuring instrument, and attribute information related to the individual and the measurement, the database storing the personal data and the attribute information as original data associated with real name information on the individual. The data distribution management device includes a usage request receiving module that receives a data usage request from a data user terminal. The relay processing device selects personal data on an individual corresponding to the data usage request from the database of each source data management device based on the data usage request that the usage request receiving module receives, and outputs the selected personal data except for real name information on the individual to the data user terminal.

The personal data distribution management system according to the present invention includes at least one source data management device, and a data distribution management device that are separate devices and are connected on a network. The source data management device includes a database that stores personal data on an individual subjected to a measurement with a measuring instrument, and attribute information related to the individual and the measurement, the database storing the personal data and the attribute information as original data associated with real name information on the individual. The data distribution management device includes a catalog management module configured to fetch the original data except for the personal data, the original data being stored in the database of each source data management device, and unify and edit the fetched data to create a data catalog.

A personal data distribution management method according to the present invention includes creating original data by associating personal data on an individual subjected to a measurement with a measuring instrument and attribute information related to the individual and the measurement with real name information on the individual and storing created data in a database, by at least one source data management device, receiving a data usage request from a data user terminal by a data distribution management device, and selecting personal data on an individual corresponding to the data usage request from the database of the at least one source data management device based on the data usage request that the data distribution management device receives, and outputting the selected personal data except for real name information on the individual to the data user terminal, by a relay processing device. The at least one source data management device, the data distribution management device, and the relay processing device are separate devices and are connected on a network.

According to these aspects of the present invention, the data distribution management device fetches original data except for personal data, and creates a data catalog. The relay processing device outputs the data, which is the data except for real name information on individuals and from the database of each source data management device based on the data usage request received from the outside, to a data user terminal. This configuration enables data distribution management that reduces the risk of information leakage of personal data and individual real name information from the database of each source data management device to the outside.

Preferably, the catalog management module of the present invention makes the created data catalog viewable on the network. This configuration publishes the catalog efficiently.

Preferably, in the present invention, the source data management device includes a re-consent processing module configured to identify an individual having personal data as a request target in accordance with an instruction from the data distribution management device in response to acceptance of the data usage request, and transmit inquiry information inquiring the individual as to whether or not to permit data provision to an information communication terminal of the individual and receive a response about whether or not to permit the data provision, and the data distribution management device includes a data output control module configured to control output of personal data of an individual who has responded not to consent to the data provision. This configuration controls the provision of personal data based on the permission or refusal of the data provision. Further, the real name information is excluded when the personal data is provided to the user, meaning that the user does not associate the real name information with the personal data.

Preferably, in the present invention, the re-consent processing module performs a first inquiry processing of instructing an inquiry about whether or not to permit data provision to an information communication terminal of a person who is involved in the measurement, and a second inquiry processing of instructing an inquiry about whether or not to permit data provision to an information communication terminal of an individual having personal data measured by the measuring instrument relating to the person who responded to consent to the data provision in the first inquiry processing. With this configuration, the first inquiry processing asks the person involved in the measurement, and the second inquiry processing is conducted to the individual having the personal data measured by the person who responded to consent to the data provision in this first inquiry processing. Given that the number of individuals is greater than the number of those involved in the measurement, setting the order of priority so as to obtain the result from the persons involved in the first inquiry processing enables efficient re-consent processing, as compared with the case of making inquiries uniformly to everyone, or in the order from individuals to the persons involved in the measurement.

Preferably, in the present invention, the source data management device has a plurality of source data management devices on the network. This configuration increases the efficiency of distributed placement of the original data.

Preferably, in the present invention, the source data management device assigns a primary pseudonym in association with the real name of each individual, and the data distribution management device includes a name identification module configured to execute a name identification process that unifies the real names of the individuals stored in the source data management devices, assigns a common secondary pseudonym to the same real names, and creates a secondary pseudonym table. When unifying the original data of the data provider management devices, this configuration sets a unified pseudonym, that is, a secondary pseudonym.

Preferably, in the present invention, the name identification module obtains the real names and primary pseudonyms from each of the source data management devices, and performs name-identification processing by matching the real names with the primary pseudonyms to create the unified secondary pseudonyms from the primary pseudonyms. This configuration creates unified secondary pseudonyms through the name identification processing by matching the real names with the primary pseudonyms.

Preferably, in the present invention, the data output control module performs deleting persons who do not consent to the application for re-consent from the secondary pseudonym table, and reassigning pseudonyms for reporting to secondary pseudonyms remaining after the deletion. This configuration changes the pseudonym for reporting even for the same data item depending on the situation of non-consent at the time of request for use, which keeps anonymity because the same pseudonym for reporting does not necessarily represent the same person.

Preferably, in the present invention, the database includes a comprehensive re-consent item allowing selection between comprehensive re-consent and each-time re-consent for a predetermined data item of the original data, the source data management device includes a data management unit that accepts settings for the comprehensive re-consent item and changes the settings, and when the setting of the comprehensive re-consent item corresponding to the data item for which the usage request has been made indicates permitted, the re-consent processing unit omits the transmission of the inquiry information about whether or not to permit data provision because the data provision is permitted. This configuration omits the work of obtaining the agreement form for those who have a comprehensive consent, which makes the procedure efficient and speedy.

Preferably, in the present invention, the data distribution management device makes the created data catalog viewable on the network. This publishes the catalog efficiently.

REFERENCE SIGNS LIST

1 Personal data distribution management system
11, 12, 13 Source data management device
110 Controller
113 Re-consent processing unit
1103 Data for provision DB (Database)
21 Measuring instrument
22 Personal terminal
30 Data distribution management device
31 Controller
311 Name-identification processing unit
312 Catalog management unit (Catalog management module)
313 Usage request receiving unit (Usage request receiving module)
314 Providing pseudonymization processing unit (Data output control module)
341 Name identification data DB
342 Data catalog DB
40 Relay processing device
50 Network
100 User terminal (Data user terminal)

The invention claimed is:

1. A personal data distribution management system comprising:
  at least one source data management device;
  a data distribution management device; and
  a relay processing device, the at least one source data management device, the data distribution management device, and the relay processing device being separate devices and being connected on a network, wherein:
  the at least one source data management device includes:
    a database that stores personal data on an individual subjected to a measurement with a measuring instrument, and attribute information related to the individual and the measurement, the database storing the personal data and the attribute information as original data associated with a personal name and a primary pseudonym associated with the personal name; and
    a data management unit that manages data transmission to the data distribution management device and the relay processing device;
  the data distribution management device includes a first memory unit that receives and stores a first data table having a pair of the personal name and a pseudonym assigned in accordance with the personal name, except for an item of the personal data, the first data table being created by the data management unit;

the relay processing device includes a second memory unit that stores a second data table by either updating or linking, the second data table having a pair of the personal data on the individual, and the pseudonym, except for an item of the personal name, the second data table being created by the data management unit; and the data distribution management device includes a usage request receiving unit that receives a data usage request from a data user terminal through the network, and, when receiving a data usage request from the usage request receiving unit, selects the personal data on the individual corresponding to the data usage request by using the second data table, extracts the pseudonym corresponding to the selected personal data on the individual from the first data table to create data for provision, and outputs the data for provision to the data user terminal.

2. The personal data distribution management system according to claim 1, wherein:

the database includes an item of contact information of an information communication terminal of the individual;

the at least one source data management device includes a re-consent processing unit configured to, when the individual is selected as a target for the data usage request, perform processing of transmitting inquiry information as to whether or not to permit data provision to the information communication terminal associated with the selected individual and processing of receiving a response about whether or not to permit the data provision;

the data distribution management device includes a data output control module configured to control output of the personal data of the individual who has responded not to consent to the data provision; and the re-consent processing unit, in accordance with a predetermined priority order, performs first inquiry processing of instructing an inquiry about whether or not to permit the data provision to the information communication terminal of a person who is involved in the measurement, and second inquiry processing of instructing an inquiry about whether or not to permit the data provision to the information communication terminal of the individual associated with the personal data measured by the measuring instrument relating to the person who responded to consent to the data provision in the first inquiry processing.

3. The personal data distribution management system according to claim 2, wherein the at least one source data management device has a plurality of source data management devices on the network.

4. The personal data distribution management system according to claim 3, wherein:

each of the plurality of source data management devices assigns the primary pseudonym in association with each individual; and the data distribution management device includes a name-identification processing unit configured to unify each personal name stored for the each of the plurality of source data management devices, assign a common secondary pseudonym to a common personal name to create a third data table, and further store the third data table in the first memory unit.

5. The personal data distribution management system according to claim 4, wherein the name-identification processing unit obtains personal names and primary pseudonyms from the each of the plurality of source data management devices, and performs name-identification processing by matching the personal names with the primary pseudonyms to create the unified secondary pseudonym from the primary pseudonyms.

6. The personal data distribution management system according to claim 4, wherein the data output control module performs deleting persons who do not consent to the application for re-consent from the third data table, and reassigning pseudonyms for reporting to secondary pseudonyms remaining after deletion.

7. The personal data distribution management system according to claim 2, wherein:

the database includes a comprehensive re-consent item allowing selection between comprehensive re-consent and each-time re-consent for a predetermined data item of the original data;

the data management unit, when receiving settings for the comprehensive re-consent item, changes the settings; and the re-consent processing unit, when determining that the settings of the comprehensive re-consent item corresponding to the data item for which the data usage request has been made indicates permitted, omits transmission of the inquiry information as to whether or not to permit the data provision.

8. A personal data distribution management method comprising:

storing, in a database, personal data on an individual subjected to a measurement with a measuring instrument, and attribute information related to the individual and the measurement, by at least one source data management device, the database storing the personal data and the attribute information as original data associated with a personal name and a primary pseudonym associated with the personal name;

receiving and storing, in a first memory unit, a first data table having a pair of the personal name and a pseudonym assigned in accordance with the personal name, except for an item of the personal data, the first data table being created by a data management unit of the at least one source data management device;

storing, in a second memory unit, a second data table by either updating or linking by a relay processing device, the second data table having a pair of the personal data on the individual, and the pseudonym, except for an item of the personal name, the second data table being created by the data management unit; and selecting, when receiving a data usage request from a data user terminal through the network by a usage request receiving unit, the personal data on the individual corresponding to the data usage request by using the second data table, extracting the pseudonym corresponding to the selected personal data on the individual from the first data table to create data for provision, and outputting the data for provision to the data user terminal, by a data distribution management device, wherein the at least one source data management device, the data distribution management device, and the relay processing device are separate devices and are connected on a network.

9. A personal data distribution management system comprising:

a plurality of source data management devices;

a data distribution management device; and a relay processing device, the plurality of source data management devices, the data distribution management device, and the relay processing device being separate devices and being connected on a network, wherein:

each of the plurality of source data management devices includes:
- a database that stores personal data on an individual subjected to a measurement with a measuring instrument, and attribute information related to the individual and the measurement, the database storing the personal data and the attribute information as original data associated with a personal name and a primary pseudonym associated with the personal name; and
- a data management unit that manages data transmission to the data distribution management device and the relay processing device;

the data distribution management device includes a first memory unit that receives and stores a first data table having a pair of the personal name and the primary pseudonym assigned in accordance with the personal name, except for an item of the personal data, the first data table being created for each of the plurality of source data management devices by the data management unit;

the relay processing device includes a second memory unit that stores a second data table by either updating or linking, the second data table having a pair of the personal data on the individual, and the primary pseudonym, except for an item of the personal name, the second data table being created for each of the plurality of source data management devices by the data management unit;

the data distribution management device includes a name-identification processing unit configured to unify each personal name of the first data table, assign a common secondary pseudonym to a common personal name to create a third data table, and further store the third data table in the first memory unit; and the data distribution management device includes a usage request receiving unit that receives a data usage request from a data user terminal through the network, and, when receiving a data usage request from the usage request receiving unit, the data distribution management device, from processing of selecting the personal data on the individual corresponding to the data usage request by using the second data table, and deleting the individual that is not a target for the data usage request from the third data table and processing of reassigning pseudonyms for reporting to secondary pseudonyms remaining after deletion, creates data for provision with the selected personal data on the individual and the pseudonyms for reporting and outputs the data for provision to the data user terminal.

* * * * *